(12) United States Patent
Barnes et al.

(10) Patent No.: US 6,394,086 B1
(45) Date of Patent: May 28, 2002

(54) INHALATION APPARATUS

(75) Inventors: Paul Barnes, King's Lynn; Wamadeva Balachandran; Wojciech Machowski, both of Guildford, all of (GB)

(73) Assignee: Bespak PLC, King's Lynn (GB)

( * ) Notice: Subject to any disclaimer, the term of this patent is extended or adjusted under 35 U.S.C. 154(b) by 0 days.

(21) Appl. No.: 09/622,342

(22) PCT Filed: Nov. 13, 1998

(86) PCT No.: PCT/GB98/03415

§ 371 (c)(1),
(2), (4) Date: Oct. 2, 2000

(87) PCT Pub. No.: WO99/42153

PCT Pub. Date: Aug. 26, 1999

(30) Foreign Application Priority Data

Feb. 20, 1998 (GB) .............................................. 9803643

(51) Int. Cl.[7] ...................... A61M 15/00; A61M 16/00; B05D 7/14; B65D 83/06
(52) U.S. Cl. ........................... 128/203.15; 128/203.12; 128/200.14; 128/200.16; 128/202.25; 239/3; 239/690; 239/706
(58) Field of Search ..................... 128/203.15, 203.12, 128/200.14, 200.16, 200.18, 200.23, 203.27, 202.25; 239/3, 690, 706, 128

(56) References Cited

U.S. PATENT DOCUMENTS

| | | | |
|---|---|---|---|
| 1,958,406 A | | 5/1934 | Darrah |
| 3,194,236 A | * | 7/1965 | Wehner ................. 128/200.14 |
| 5,267,555 A | * | 12/1993 | Pajalich ................ 128/200.14 |
| 5,474,059 A | * | 12/1995 | Cooper ................. 128/200.22 |
| 5,483,953 A | * | 1/1996 | Cooper ................. 128/200.14 |
| 5,511,726 A | | 4/1996 | Greenspan et al. |
| 5,515,841 A | * | 5/1996 | Robertson et al. ..... 128/200.16 |
| 5,694,920 A | * | 12/1997 | Abrams et al. ........ 128/200.16 |
| 5,743,251 A | * | 4/1998 | Howell et al. ........ 128/200.14 |
| 5,881,716 A | * | 3/1999 | Wirch et al. .......... 128/200.16 |
| 5,894,841 A | * | 4/1999 | Voges .................... 128/203.12 |
| 5,915,377 A | * | 6/1999 | Coffee .................. 128/200.14 |
| 6,014,970 A | * | 1/2000 | Ivri et al. .............. 128/200.16 |
| 6,068,199 A | * | 5/2000 | Coffee .................. 128/203.12 |
| 6,079,634 A | * | 6/2000 | Noakes et al. ........ 128/200.14 |
| 6,105,571 A | * | 8/2000 | Coffee .................. 128/200.14 |

FOREIGN PATENT DOCUMENTS

| | | |
|---|---|---|
| WO | WO 94/14543 | 7/1994 |
| WO | WO 94/19042 | 9/1994 |
| WO | WO 96/40441 | 12/1996 |

* cited by examiner

Primary Examiner—John G. Weiss
Assistant Examiner—Darwin Erezo
(74) Attorney, Agent, or Firm—Smith, Gambrell & Russell

(57) ABSTRACT

This invention relates to an inhalation apparatus for dispensing an inhalable substance and, in particular, but not exclusively, to an apparatus for use in the delivery of therapeutic substances to the human lung. There is provided and apparatus for dispensing an aerosol of electrostatically charged droplets including a housing having an open end duct in which are located a first electrode having an upper surface lying in a generally longitudinal plane of the duct and a second electrode spaced from the first electrode. The apparatus further includes means for delivering a metered quantity of liquid to the upper surface of the first electrode for atomization, and charging means for applying a higher potential to the second electrode with respect to the first electrode to effect atomization.

11 Claims, 1 Drawing Sheet

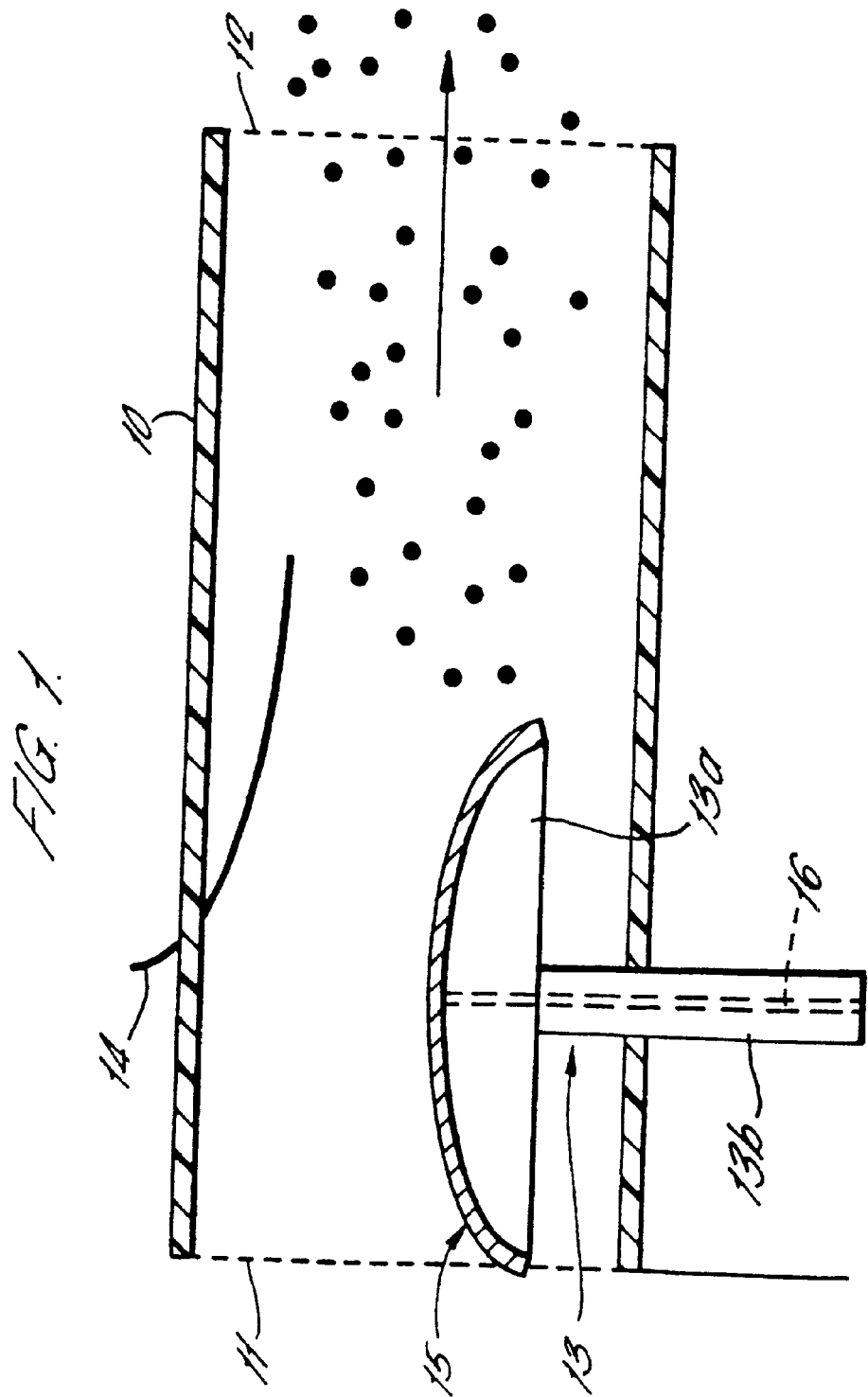

INHALATION APPARATUS

BACKGROUND OF THE INVENTION

This invention relates to inhalation apparatus for dispensing an inhalable substance and in particular, but not exclusively, to apparatus for use in the delivery of therapeutic substances to the human lung.

Medicinal inhalers are well known and have made a significant contribution to ailments such asthma. Of particular usefulness are hand-held metered dose inhalers and dry powder inhalers. Each produces an aerosol of fine particles containing medicament and which are carried into the respiratory system as a user inhales.

Several factors are known to effect the site at which deposition of such airborne particles are deposited in the respiratory system. Research has revealed that the electrostatic charge on the particles plays a very important part in determining the site of deposition and it has been shown that the level of electrostatic charge can be used to control particularly the site of deposition. A site may thereby be selected which is higher or lower in the bronchial tree to meet requirements of a particular therapeutic or diagnostic procedure. The level of charge can also serve to reduce the amount of particles lost through exhalation and this is particularly important where small quantities of medicament are delivered.

One means of achieving this is found in WO-A-94/19042 which describes dispensing apparatus for discharging a metered dose of a liquid in aerosol form from a pressurised dispensing container. The droplets are propelled through a passageway towards an inhalation port passing through a charging region.

The charging region contains one electrode which has at least one pointed feature and a second electrode having co-operating features of relatively low curvature. The aerosol emerging from the apparatus will carry an inherent level of electrostatic charge. The charge can be modified in a controlled manner by imparting further electrostatic charges to the particles as they pass through the charging region before being inhaled.

For certain applications it is desired to use electrostatic forces for generating an aerosol of electrically charged droplets particularly of a much smaller amount of liquid such as a single drop, which the above described apparatus would be unable to achieve.

EP-A-0224352 describes a method of generating a charged spray for ocular treatment. The formulation is supplied to a hollow spray nozzle which has an opening of such small cross-section as to retain up to 20 μl of the formulation by surface tension. A metered dose of the formulation is supplied to the nozzle, after which a piston is activated to provide a current of air to force the formulation out of the nozzle. At the same time a high voltage is applied to a region of the nozzle in contact with the formulation causing the atomisation of the liquid to form a spray of electrically charged droplets for application to an eye.

This method thus requires the use of coordination of moving parts (the piston) and the triggering of the voltage.

U.S. Pat. No. 5,511,726 discloses a portable nebuliser capable of producing a finely divided aerosol having uniformly sized droplets. The nebuliser includes a source of fluid such as a capillary tube coupled to a fluid reservoir to which a high voltage is supplied in order to generate the aerosol by electrical atomisation. The nebuliser further includes a means for mechanical positive displacement of fluid control for controlling the amount of fluid atomised. One object of the present invention is to obviate the need for moving parts and to provide apparatus which is able to atomise a small quantity of liquid such as a single drop of liquid using electrostatic forces alone.

BRIEF SUMMARY OF THE INVENTION

The invention therefore provides apparatus for dispensing an aerosol of electrostatically charged droplets comprising a housing in which are located a first electrode and a second electrode spaced from the first electrode, the apparatus further comprising means for delivering a metered quantity of liquid to an upper surface of the first electrode for atomisation and charging means for applying a higher potential to the second electrode with respect to the first electrode to effect atomisation, characterised in that the first and second electrodes are located in an open ended duct, the upper surface of the first electrode lying in a generally longitudinal plane of the duct, wherein the upper surface of the first electrode is shaped such that liquid delivered onto the upper surface of the first electrode spreads out over the surface of the first electrode causing a greater build-up of liquid around a perimeter of said first electrode than elsewhere on the first electrode.

BRIEF DESCRIPTION OF THE FIGURE

A preferred embodiment of the present invention will now be described, by way of example only, and with reference to the accompanying drawings in which:

FIG. 1 is a cross-section of a side elevation of the atomising section of dispensing apparatus according to the present invention.

DETAILED DESCRIPTION OF THE INVENTION

The dispensing apparatus of the present invention includes a housing (not shown) having an atomising section shown in FIG. 1. The atomising section includes a horizontally extending cylindrical duct 10 which is open at both ends through which air can flow. One end defines an air inlet 11 and the other defines or communicates with an inhalation port 12 suitable for oral inhalation.

Located within the cylindrical duct 10 is a first electrode 13, which is preferably mushroom shaped having an annular head 13a with a gently convexly curved upper surface 15. The first electrode is positioned so that the head 13a lies substantially in a longitudinal direction in the duct 10. The first electrode 13 is preferably earthed via the stem 13b of the electrode 13 which protrudes from the duct 10.

Also located within the cylindrical duct 10 is a second electrode 14, which second electrode 14 is connected to a charging circuit capable of applying a potential to the second electrode 14 greater than that of the first electrode 13 of 10 to 20 kV. The second electrode 14 is preferably a single wire, the point of entry of which into the duct 14 is offset in a longitudinal direction from the axis of the stem 13b of the first electrode 13. Typically the electrodes are 0.5 to 5 cm apart at the closest point. The second electrode 14 may be completely enclosed in an insulating material thereby mechanically shielding the electrode 14 from the patient and any objects inserted into the mouthpiece 12.

The housing further houses means (not shown) for delivering liquid to the first electrode 13, either directly to the upper rounded surface 15 or via a channel 16 through the stem 13b of the mushroom. The delivery means include metering apparatus to meter a small quantity of the liquid, such as a single drop of preferably between 20–50 $\mu$l, or possibly more, of the liquid to be dispensed.

The liquid to be dispensed is preferably ethanol based and may be a water/ethanol mixture of up to 60% by volume concentrate of ethanol. However, other liquids may be selected which are suitable for inhalation and which can be successfully atomised in stable electrohydrodynamic mode. Such liquids must preferably have a high resistivity and low surface tension and also preferably low permittivity. The preferred range of resistivity is between $7.6\times10^3$ to $1\times10^8$ $\Omega$m and the preferred maximum surface tension is 0.04 N/m.

The housing further houses a charging circuit and power supply battery. The battery is electrically connected by means of appropriate wiring to the second electrode 14.

In use a metered quantity, such as a drop of liquid is delivered to the first electrode 13. Due to the low surface tension of the liquid it spreads out over the surface of the first electrode 13. Gravitational forces cause a greater build-up of liquid around the perimeter of the head 13*a* than elsewhere on the head. The charging circuit is energised to apply a DC voltage of 10 to 20 kV to the second electrode 14. The resulting electric field at the edge of the first electrode 13 causes the liquid to atomise at the periphery of the mushroom electrode 13 in the form of atomised droplets. The atomisation of the liquid takes place only on the edge of the head 13*a* and the strong ionic wind created by the end of the second electrode 14 forces the spray of highly charged droplets produced during the electrostatic atomisation along the cylinder 10 at a low velocity to the mouthpiece 12 without any additional air flow. Once all the liquid has been atomised, the charging circuit is switched off.

Further means may be provided to modify the charge on the droplets, to reduce, enhance, neutralise or reverse the charge.

In alternative embodiments of the present invention the second electrode 14 may be provided in the form of a mesh located above the first electrode 13. Alternatively, it could be in the form of a ring, an elipse or a squashed elipse with the wires touching. The first electrode may also be made of or covered with a porous material.

The potential applied to the second electrode 14 is preferably selected to minimise droplet deposition on the second electrode 14. However it is also possible to include a means of providing additional air flow to help reduce this deposition.

A further embodiment of the invention can be used to atomise a continuous stream of liquid for use in a nebuliser.

In this embodiment the delivery means continuously supply liquid to the first electrode 13 to replace the atomised liquid while continually applying potential to the electrode 14.

What is claimed is:

1. Apparatus for dispensing an aerosol of electrostatically charged droplets comprising a housing in which are located a first electrode (13) and a second electrode (14) spaced from the first electrode, the apparatus further comprising means for delivering a metered quantity of liquid to an upper surface (15) of the first electrode for atomisation and charging means for applying a higher potential to the second electrode with respect to the first electrode to effect atomisation, characterised in that the first and second electrodes are located in an open ended duct (10), the upper surface of the first electrode lying in a generally longitudinal plane of the duct, wherein the upper surface of the first electrode is shaped such that liquid delivered onto the upper surface of the first electrode spreads out over the surface of the first electrode causing a greater build-up of liquid around a perimeter of said first electrode than elsewhere on the first electrode.

2. Apparatus as claimed in claim 1 in which the potential difference between the electrodes (13, 14) is between 10 and 20 kV.

3. Apparatus as claimed in claim 1, in which the first electrode (13) is earthed.

4. Apparatus as claimed in claim 1, in which the first electrode (13) comprises a head **(13*a*), having a convexly curved surface (15) and a stem (13*b*)** projecting therefrom.

5. Apparatus as claimed in claim 4, in which the first electrode (13) is mushroom shaped.

6. Apparatus as claimed in claim 4, in which the delivery means delivers liquid to the upper surface (15) of the first electrode (13) via a channel (16) in the stem **(13*b*)**.

7. Apparatus as claimed in claim 1 in which the second electrode (14) is a single wire.

8. Apparatus as claimed in claim 7, in which the second electrode (14) enters the duct (10) at an entry point offset in a longitudinal direction with respect to an axis through the centre of the upper surface (15) of the first electrode (13).

9. Apparatus as claimed in claim 1, in which the second electrode (14) is insulated.

10. Apparatus as claimed in claim 1 in which means are provided downstream of the first electrode (13) and second electrode (14) to modify the charge on the atomised droplets.

11. Apparatus as claimed in claim 1 in which the delivery means continuously delivers a metered quantity of liquid to the first electrode (13) for dispensing a continuous aerosol.

* * * * *